United States Patent [19]

Azuma et al.

[11] Patent Number: 4,873,092
[45] Date of Patent: Oct. 10, 1989

[54] SLOW-RELEASING PREPARATION

[75] Inventors: Ichiro Azuma; Seiichi Tokura, both of Sapporo; Shinichiro Nishimura, Sapporo; Hiroshi Seo, Souka, all of Japan

[73] Assignee: Murata Kikai Kabushiki Kaisha, Kyoto, Japan

[21] Appl. No.: 53,072

[22] Filed: May 21, 1987

[51] Int. Cl.⁴ .................................................. A61K 9/50
[52] U.S. Cl. ....................................... 424/499; 424/422
[58] Field of Search ................................ 424/499, 422

[56] References Cited

U.S. PATENT DOCUMENTS 3,914,413 10/1975 Balassa .............................. 424/95 X
4,457,918 7/1984 Holick et al. ........................... 514/25
4,532,134 7/1985 Malette et al. ......................... 424/95
4,659,700 4/1987 Jackson ................................. 514/55

FOREIGN PATENT DOCUMENTS 0021750 1/1981 European Pat. Off. ............. 536/20

Primary Examiner—Thurman K. Page
Attorney, Agent, or Firm—Spensley, Horn, Jubas & Lubitz

[57] ABSTRACT

A slow-releasing preparation comprises porous granules of deacetylated chitin as a carrier and a physiologically active substance contained in the granules. The slow-releasing prepartion can be embedded in a body for curing diseases.

11 Claims, 2 Drawing Sheets

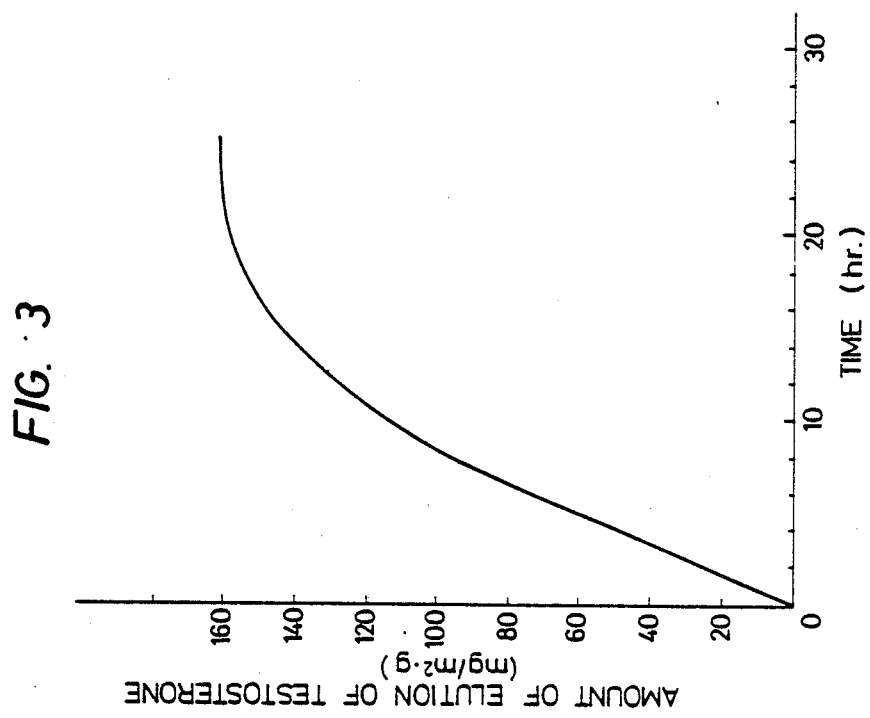

SLOW-RELEASING PREPARATION

FIELD OF THE INVENTION AND RELATED ART STATEMENT

This invention relates to medicines or medical service and more particularly, to slow-releasing preparations which can reduce the toxicity and side effects of known drugs and can continue the physiological efficacy over a long time, thus being useful in curing diseases.

In recent years, intensive studies have been made on chemotherapeutics and immunochemotherapeutics. For curing cancer, anticancer drugs are commercially sold, but most of them have high toxicity and side effects with cardio-toxicity in some instances. This leads to the disadvantage that the concentration of these drugs cannot be increased upon their application.

In an ordinary manner of administration, when a drug is dosed, the concentration in blood increases, so that side effects such as cardio-toxicity develop. To avoid this, it is the usual practice to suppress the concentration to a minimum and repeat the dosage at short-time intervals. With drugs for the endocrine system such as hormone drugs as well, there is a demand for preventing side effects upon administration of the drugs at high concentrations.

As is known in the art, chitin, which is a polysaccharide having N-acetyl-D-glucosamine-$\beta$-1,4-glucosido bonds, is contained in crustaceans such as crabs and shrimps and insects such as locusts and beetles and occurs as widely distributed in the natural field. Chitin and chitosan, which is deacetylated chitin obtained by thermally treating chitin with a concentrated caustic alkali to hydrolyze the acetyl groups, have been utilized for slow release of drugs. For instance, Youichi Sawayanagi et al read a paper, entitled "Increase in Elution of Sparingly Soluble Medical Substances by Milling in Mixing with Chitin and Chitosan", in the 102nd annual convention of the Japanese Association of Pharmacy (1982) and Fukushi Higashide et al also read a paper, entitled "Study on a Milling an Mixing Method for the Slow Release of Medical Substances Using Chitin and Chitosan", in the 103th annular convention of the Japanese Association of Pharmacy (1983). In these papers, studies were made on the elution of sparingly soluble medical substances in which chitin, chitosan or crystalline cellulose was milled by mixing with medical substances and tabletted. In the 103th annual convention of the Japanese Association of Pharmacy (1983), Hideo Takenaka et al presented a paper, entitled "Application of Chitosan to Slow-releasing Preparation of Aspirin", in which the property of chitosan being gelled in a dilute acid aqueous solution is utilized, and aspirin is added to the gel and shaped into granules and tablets by a wet process to determine the ability of elution of the aspirin.

In the 104th annual of the Japanese Association of Pharmacy (1984), Fukushi Higashide et al investigated and reported, in "Study of Chitin and Chitosan as Additives for Enzyme-Fixing Tablets—Relating to Alpha-Amylase", the relation between elution of medical substances and the manner of milling or grinding which is determined by mixing and milling chitin or chitosan and a medical substance and shaping the mixture into granules.

As stated above, although the possibility of utilizing chitin or chitosan as a slow-releasing preparation has been heretofore suggested, a third component such as gelatin is necessary in order to mix chitin or chitosan with medical substances and shape the mixture into granules or tablets. In view of the acid and alkali resistances of chitin and chitosan, limitation is placed on the choice of the third component. Especially, when the slow-releasing preparation is utilized by embedment in a body, such a third component may disadvantageously give a danger of the life.

OBJECT AND SUMMARY OF THE INVENTION

It is an object of the present invention to provide a slow-releasing preparation which can be embedded in a body for curing diseases.

It is another object of the present invention to provide a new carrier on which a drug, e.g. an anticancer drug or hormone drug, may be applied.

The present inventors made porous granules of deacetylated chitin and provide the granules as a carrier on which a drug, e.g. an anticancer drug or a hormone drug, was applied, thereby obtaining a slow-releasing preparation. It was found that thus obtained preparation could be embedded in a body for curing diseases.

BRIEF DESCRIPTION OF THE DRAWINGS

FIGS. 2 and 3 are, respectively, graphs showing a change in amount of the elution of testosterone from each of the preparations in other examples in relation to time.

DETAILED DESCRIPTION OF PREFERRED EMBODIMENTS

Figure 2:
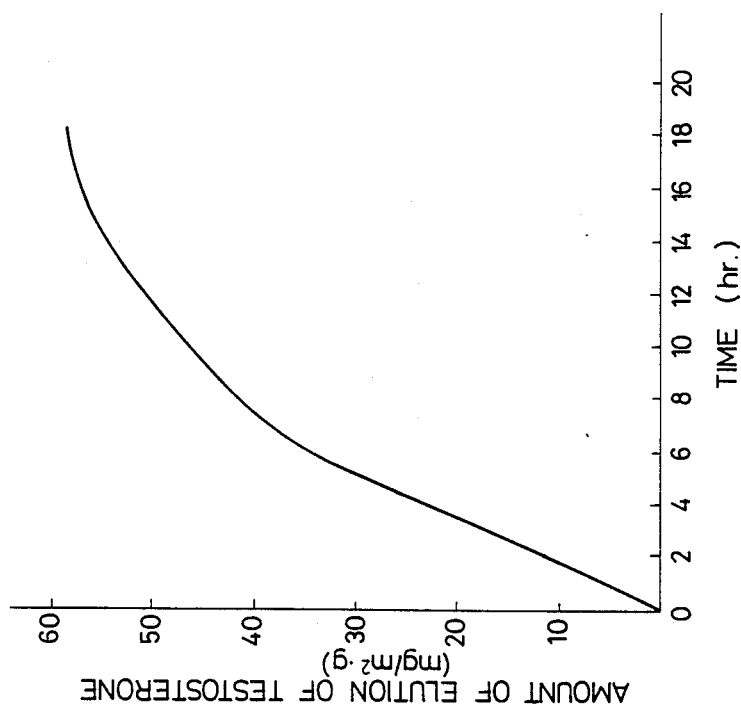

The carrier used in the practice of the invention is in the form of porous granules of deacetylated chitin. These granules may be those which are prepared from deacetylated chitin according to the process disclosed by the present inventors in U.S. application Ser. No. 07/011,150 or may be those which are again controlled with respect to the degree of deacetylation.

The chemical structure of chitin is represented as poly-N-acetylglycosamine. It has been reported in "Chitin" issued by Pergamon Press and Polymer Journal 15, No. 597 (1983) that chitin obtained by extracting natural chitin compound is generally deacetylated in 5–10%.

The deacetylated chitin means a substance obtained by further deacetylating chitin. More particularly, the aminoacetyl groups of chitin are deacetylated into amino groups. The degree of deacetylation (hereinafter abbreviated as DA) is in the range of $0 < DA < 100\%$. Arbitrarily deacetylated chitin may be obtained by suitably controlling the deacetylation treatment of chitin. The deactylated chitin carrier used in the present invention may be obtained by controlling the DA at a desired level and shaping the resultant deacetylated chitin into porous granules, or by forming, into porous granules, deacetylated chitin having a DA range within which it is more likely to shape and controlling the DA of the formed porous granules.

The deactylated chitin in the form of the porous granules according to the invention may be obtained, as described in the afore-indicated patent application, by dissolving 2–20 wt% of low molecular weight chitosan having, preferably, an average molecular weight of 10,000 to 230,000 in an acidic aqueous solution, and dropping the solution into a basic solution whereupon granular, porous chitosan is coagulated and precipitated. The granular, porous chitosan obtained as mentioned above may be acetylated by using acetic anhydride to produce granular, porous deacetylated chitin which has desirable DA.

The thus obtained deacetylated chitin is in the form of porous granules which have uniform, fine, continuous cells throughout the granules. The granule size, pore size and specific surface area are optimumly determined by selection of the conditions in the process set forth before while taking into account the strength and the slow-releasing velocity of a drug to be contained. The porous granules should be washed sufficiently with ethyl alcohol or the like so that they are utilized for medical service, after which they are used in an arbitrary condition such as a wet condition or a swollen condition after drying.

As described above, the present invention contemplates to provide a slow-releasing preparation which comprises a carrier of deacetylated chitin with a desired level of DA in the form of porous granules having selected granule size, pore size and specific surface area, and a physiologically active substance, such as an anticancer drug or a hormone drug, contained in the carrier. The physiologically active substance may be, aside from the anticancer drugs and the hormone drugs, anti-epileptic drugs, antiemetics, pyschotropic drugs, antispastics, cardiotinics, antiarrhythmic agents, angiotonics vasodilators, sulfur drugs and the like.

The use of deacetylated chitin as a carrier for medical substances is reported, apart from the aforedescribed reports, by the present inventors in "Vaccine", Vol. 2, 93 (1984). In this report, mice are intracutaneously dosed with a mixed solution of cancer cells (Meth-A fibrosarcoma cells) and deacetylated chitin to determine a survival rate after 4 weeks. Moreover, a solution of the same type as used above is repeatedly dosed to determine a survival rate after 2 weeks. As a result, it is found that any antibody is not formed in the antitumor mouse body with respect to the deacetylated chitin. In other words, with the deacetylated chitin having a range of 0<DA<100%, it has not only no antibody product, but also an effect of enhancing the immune activity, thus being considered to be a suitable material as a carrier for adsorption of drugs.

The slow-releasing property of the preparation according to the invention in which porous granules of deacetylated chitin are used as a carrier is considered to develop as follows: when the preparation is intracutaneously dosed, is embedded or is dosed in a body by other suitable methods, activated macrophages gradually gormandize the deactylated chitin. On the other hand, remaining aminoacetyl groups or neighbours thereof are hydrolyzed with lysozyme. As a result, the drug is slowly released to show the slow-releasing effect.

The present inventionn is illustrated by way of examples. The measurement of a degree of deacetylation (DA) was determined from a calibration curve by determining a ratio of absorption intensities at 1655 cm$^{-1}$ and 2867 cm$^{-1}$ using an infrared spectrophotometer.

EXAMPLE 1

Deacetylated chitin having an average molecular weight of 46,000 and a DA value of 80%, that is, chitosan, was dissolved in dichloroacetic acid and water at a concentration of 6% to give a deacetylated chitin solution. This solution was dropped for coagulation into a mixed basic aqueous solution of 5% of caustic soda, 50% of methanol and water from a nozzle with a diameter of 0.15 mm under a nitrogen gas pressure of 2 kg/cm$^2$, thereby obtaining porous granules, followed by washing sufficiently with water.

555 mg (on a dry basis) of the thus obtained porous granules of the deacetylated chitin having a DA value of 80%, a granule size of 42–80 mesh, a pore size of 0.4 micrometers and a specific surface area of 30.9 m$^2$/g was suspended in 50 ml of deionized water, to which 10 mg of an anticancer drug, Adriacin, (registered trade mark, made by Kyowa Hakkou K.K. and hereinafter referred to as ADM hydrochloride) was added, followed by agitation at room temperature under reduced pressure for 4 hours. After heating up to 30° C. and evaporation to dryness, 50 ml of water was again added, followed by filtration, washing twice each with 20 ml of water, washing with 20 ml of ethyl alcohol, drying in air, and finally drying under vacuum at 40° C. to obtain a preparation in which the ADM hydrochloride was contained in the porous granules of the deacetylated chitin. The granules were packed in a small column, through which an eluting solution having 20 μg/ml of egg white lysozyme in a physiological saline solution was passed at 37° C. and at a flow rate of 0.3 ml/minute. The slow-releasing elution of the ADM hydrochloride was quantitatively determined with time using an absorbance at 458 mμ, with the results shown in FIG. 1.

EXAMPLE 2

The general procedure of Example 1 was repeated except that the basic aqueous solution into which the deacetylated chitin solution was dropped for coagulation was a mixed aqueous solution of 2% caustic soda, 60% of methanol and water, thereby obtaining porous granules of the deactylated chitin having a DA value of 80%, a granule size of 20–40 mesh, a pore size of 0.3 micrometers and a specific surface area of 49.7 m$^2$/g. 40 g (on a wet basis) of the granules was suspended in 150 ml of methyl alcohol and allowed to stand for 30 minutes, followed by removal by filtration and re-suspension in 150 ml of ethyl alcohol. The above procedure was repeated three times and, after dehydration, the granules were suspended in 150 ml of ethyl alcohol, to which 20 mg/ml of testosterone (made by Fluka A.G.), which is a male hormone, and 5 ml of ethyl alcohol were added. The mixture was shaken at room temperature under reduced pressure and after 2 hours, was concentrated and evaporated to dryness at 30° C., followed by washing with 150 ml of ethyl alcohol and concentration and drying under reduced pressure to obtain a preparation in which the male hormone was incorporated in the porous granules of the deacetylated chitin.

The granules were packed in a small column, through which an eluting solution containing 20 μg/ml of egg white lysozyme in a physiological saline solution was passed at a flow rate of 0.2 ml/minute to quantitatively determine a slow-releasing elution of the testosterone using an absorbance at 238 mμ. The results are shown in FIG. 2.

EXAMPLE 3

40 g (on a wet basis) of the porous granules of the deacetylated chitin used in Example 2 was suspended in 50 ml of methyl alcohol and allowed to stand for 30 minutes, followed by filtration to remove the methyl alcohol. The above procedure was repeated three times and the granules were subsequently suspended in 100 ml of ethyl alcohol, to which 5 ml of acetic anhydride, followed by shaking at room temperature for 1 hour, filtering to remove the reaction solution, washing ten times each with 30 ml of ethyl alcohol, and drying to obtain porous granules. The porous granules had a DA value of from 5% in the vicinity of the surface to 72% in the inside of the granules, a granule size of 40-80 mesh, a pore size of 0.2 μm and a specific surface area of 20.13 m$^2$/g.

Thereafter, a preparation containing testosterone, which is a male hormone, was obtained in the same manner as in Example 2. The slow-releasing property was tested in the same manner as in Example 2, with the results shown in FIG. 3.

Figure 1:
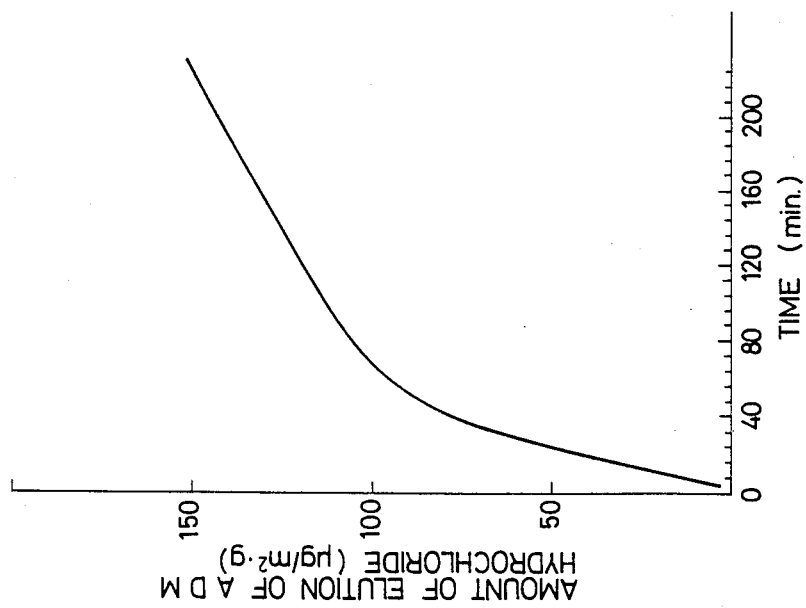
FIG. 1 is a graph showing a change in amount of the elution of ADM hydrochloride from a preparation of the invention in relation to time.

As will be apparent from FIG. 1 which shows the results of Example 1, after release of the drug from the carrier surface, it is slowly released from the pores with time. Accordingly, the preparation can be satisfactorily utilized as the anticancer drug. When FIG. 2 showing the results of Example 2 is compared with FIG. 3 showing the results of Example 3, both indicate the slow-releasing property but the slow-releasing elution of the medical substance proceeds more rapidly in the case of FIG. 3 than in the case of FIG. 2. This is considered due to the fact that the surfaces of the porous granules are acetylated and are caused to be hydrolyzed with lysozyme more rapidly. This means that the rapid effect on a local site can be brought about by changing the state of the carrier. Accordingly, when the porous granules of the deacetylated chitin are provided as a carrier in which an anticancer drug or a hormone drug is incorporated and the resultant preparation is embedded in a body for curing diseases, the embedded ring contained in the porous granules is released over a long term at a constant concentration to a local site which is a lesion. By this, the problems of toxicity and side effects can be significantly reduced while showing the curing effect.

In case where a drug alone is dosed, the concentration in the blood increases transiently with the attendant disadvantage that there is a high possibility of a danger to the life and the strength cannot be enhanced. As a result, the metabolic rate becomes high with deactivation within a short time, so that a next administration has to be made at a shorter interval.

Adriamycin, which is one of anticancer drugs, has a LD50 value (mouce) of 9.8 mg/kg and is thus high in toxicity. Up to now, this drug has been hitherto dosed to only patients in the terminal stage life. Additionally, it has been reported that in order to suppress the side effect, the dosage should be stopped for 7 to 18 days.

On the other hand, when a slow-releasing preparation containing a drug in the carrier of the deacetylated chitin in the form of porous granules according to the invention is used, the drug is released at a constant concentration to a local side and its activity continues over a long time. The interval before a next administration is prolonged, so that physiological and physical pains given to patients can be mitigated.

What is claimed is:

1. A slow-releasing preparation consisting essentially of porous granules of deacetylated chitin as a carrier and at least one physiologically active therapeutic substance contained in the granules, wherein said therapeutic substance is selected from the group consisting of an anticancer drug, a hormone drug, an antiepileptic drug, an antiemetic, a psychotropic drug, an antispastic, a cardiotonic, an antiarrhythmic agent, an angiotonic, a vasodilator, and a sulfur drug.

2. A slow-releasing preparation according to claim 1, wherein the porous granules of the deacetylated chitin have a controlled degree of deacetylation of the porous granules obtained from deacetylated chitin.

3. A slow-releasing preparation according to claim 2, wherein the degree of deacetylation of said porous granules is 5-80%.

4. A slow-releasing preparation according to claim 1, wherein said porous granules of deacetylated chitin are obtained by dissolving low molecular weight deacetylated chitin in an acidic aqueous solution and dropping the solution into a basic solution whereupon granular, porous deacetylated chitin is coagulated and precipitated.

5. A slow-releasing preparation according to claim 4, wherein said basic solution is a mixed basic aqueous solution comprising caustic soda, methanol and water.

6. A slow-releasing preparation according to claim 1, wherein said porous granules of deacetylated chitin are obtained by dissolving low molecular weight chitosan in an acidic aqueous solution, dropping the solution into a basic solution whereupon granular, porous chitosan is coagulated and precipitated, and acetylating the granular, porous chitosan to obtain the porous granules of deacetylated chitin.

7. A slow-releasing preparation according to claim 1, wherein said slow-releasing preparation is one that may be embedded in a body for curing diseases.

8. A slow-releasing preparation according to claim 1, wherein said physiologically active substance is an anticancer drug.

9. A slow-releasing preparation according to claim 1, wherein said physiologically active substance is a hormone drug.

10. A slow-releasing preparation according to claim 1, wherein said porous granules have uniform, fine, continuous cells throughout the granules.

11. A slow-releasing preparation according to claim 6, wherein said low molecular weight chitosan has an average molecular weight of 10,000 to 230,000.

* * * * *

UNITED STATES PATENT AND TRADEMARK OFFICE
CERTIFICATE OF CORRECTION

PATENT NO. : 4,873,092
DATED : October 10, 1989
INVENTOR(S) : Ichiro Azuma, et al.

It is certified that error appears in the above-identified patent and that said Letters Patent is hereby corrected as shown below:

ON TITLE PAGE:
After "[73] Assignee:", delete "Murata Kikai Kabushiki Kaisha, Kyoto, Japan", and substitute therefor --Fuji Spinning Co., Ltd., Tokyo, Japan--.

Signed and Sealed this

Twenty-second Day of October, 1991

Attest:

HARRY F. MANBECK, JR.

*Attesting Officer*      *Commissioner of Patents and Trademarks*